(12) United States Patent
Holdaway et al.

(10) Patent No.: US 6,623,456 B1
(45) Date of Patent: Sep. 23, 2003

(54) NEEDLE MEMBER WITH OFF-SET FLASH CHAMBER AND/OR DISPLAY MEMBER

(75) Inventors: Richard G. Holdaway, Storrs, CT (US); P. Spencer Kinsey, Vernon, CT (US)

(73) Assignee: Bio-Plexus, Inc., Vernon, CT (US)

( * ) Notice: Subject to any disclaimer, the term of this patent is extended or adjusted under 35 U.S.C. 154(b) by 0 days.

(21) Appl. No.: 09/807,562

(22) PCT Filed: Oct. 15, 1999

(86) PCT No.: PCT/US99/24254

§ 371 (c)(1),
(2), (4) Date: Apr. 12, 2001

(87) PCT Pub. No.: WO00/23131

PCT Pub. Date: Apr. 27, 2000

Related U.S. Application Data

(60) Provisional application No. 60/104,531, filed on Oct. 16, 1998, and provisional application No. 60/104,537, filed on Oct. 16, 1998.

(51) Int. Cl.[7] ............................................. A61M 5/178
(52) U.S. Cl. .................... 604/164.08; 604/198; 604/264
(58) Field of Search .................................. 604/158, 161, 604/164.01, 164.02, 164.08, 167.02, 167.06, 168.01, 170.01, 170.02, 198, 263, 264

(56) References Cited

U.S. PATENT DOCUMENTS

| | | | | | |
|---|---|---|---|---|---|
| 5,120,319 A | * | 6/1992 | Van Heugten et al. | .. | 604/168.01 |
| 5,137,518 A | * | 8/1992 | Mersch | ................... | 604/168.01 |
| 5,540,662 A | * | 7/1996 | Nicholson | .................... | 604/110 |
| 5,665,072 A | * | 9/1997 | Yoon | ..................... | 604/164.12 |
| 5,697,914 A | * | 12/1997 | Brimhall | ................ | 604/164.01 |
| 6,270,480 B1 | * | 8/2001 | Dorr et al. | ................... | 604/115 |

* cited by examiner

Primary Examiner—Edward K. Look
Assistant Examiner—John K Fristoe, Jr.
(74) Attorney, Agent, or Firm—Knobbe, Martens, Olson & Bear, LLP

(57) ABSTRACT

A needle assembly (10) for insertion or removal of fluids has a housing (20) that defines a flash chamber (64) that is radially offset from the longitudinal axis of the needle. An enhanced surface area display member (80) can be installed in an observable location in a needle housing (20) to facilitate observation of the fluid therein.

14 Claims, 7 Drawing Sheets

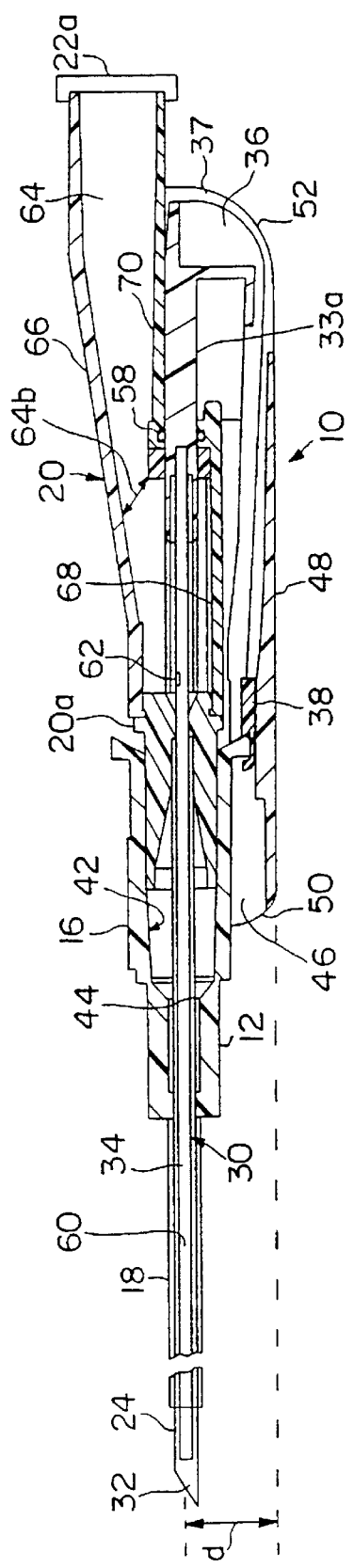
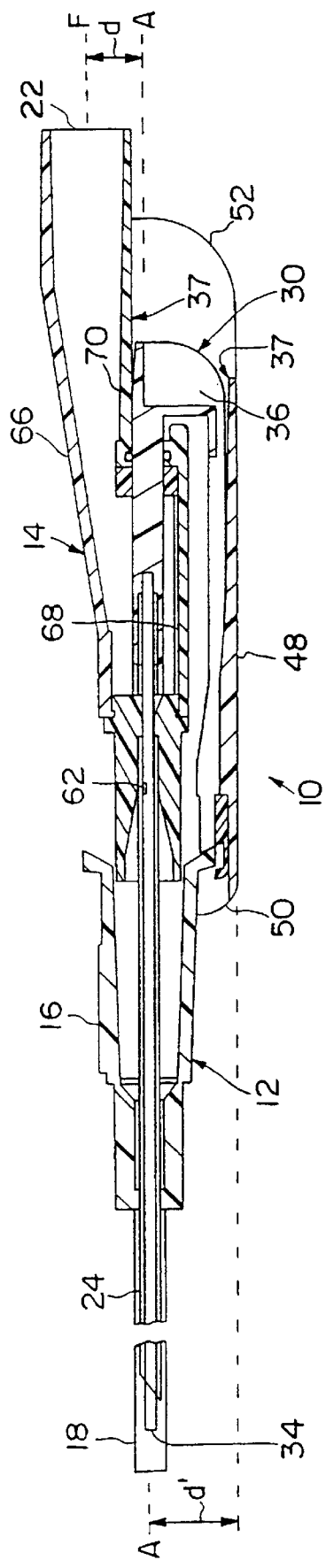

NEEDLE MEMBER WITH OFF-SET FLASH CHAMBER AND/OR DISPLAY MEMBER

CROSS REFERENCE TO RELATED APPLICATION

This application claims the benefit of U.S. provisional application No. 60/104,531, filed Oct. 16, 1998 and from U.S. provisional application No. 60/104,537, filed Oct. 16, 1998.

BACKGROUND OF THE INVENTION

1. Field of the Invention

The present invention relates to a needle member especially suited for use as a hypodermic needle and for use with a catheter. More particularly, the present invention relates to a needle member that includes a flash chamber for the detection of fluid therein.

2. Related Art

Needle and catheter arrangements for removal or insertion of fluids through the epidermis of a patient are well known. Healthcare workers using needles and catheters often have difficulty in accurately locating and puncturing a vein inside a patient, making necessary multiple insertions of the needle which cause discomfort to the patient. One mechanism to aid in locating veins is a flash chamber, a clear or translucent chamber located behind the proximate end of the cannula, allowing the user to see the blood as it exits the needle. This first showing of blood is called "flash". By watching for flash, the user can verify that the tip of the hypodermic needle has entered the vein and thus the user can cease penetration of the patient's flesh before the distal end of the needle penetrates the far side of the vein.

Another aid to healthcare workers attempting accurate placement of cannulae is a hypodermic needle which allows insertion at a wide range of angles, especially angles in which the hypodermic needle is substantially parallel to the epidermis of the patient.

Yet a third feature which aids venipuncture is a catheter and hypodermic needle arrangement which is modular and allows easy addition and removal of accessories as required.

U.S. Pat. No. 5,009,642 to C.R. Sahi, dated Apr. 23, 1991 and entitled "SELF-BLUNTING NEEDLE ASSEMBLY WITH A CATHETER, AND CATHETER ASSEMBLY USING THE SAME", discloses a self-blunting needle assembly (10) for use with a catheter (40). The needle assembly (10) includes a needle (12) that comprises a transparent fluid collection tube (or "flash chamber") (24) secured to a needle shaft (14) (see FIG. 4). The needle (12) also includes an elongate probe (30) movably disposed within the needle shaft (14). Prior to use, the catheter is placed over the needle shaft and is positioned to engage the probe. The needle shaft is then used to introduce the catheter into a vein. When venipuncture is achieved, blood flows through the needle shaft into the collection tube, giving the user a visual indication that the needle and catheter are properly positioned. The needle assembly can then be withdrawn to allow use of the catheter in a conventional manner. Since the catheter engages the probe, withdrawal of the needle member from the catheter advances the probe within the needle so that the withdrawn needle assembly becomes blunted after having been used. The collection tube and needle shaft are both generally cylindrical in configuration and are co-axially disposed relative to each other. The diameter of the collection tube, however, is several times greater than the diameter of the needle shaft and catheter, so that the collection tube limits the angles at which the needle may be introduced into the patient's vein.

U.S. Pat. 5,374,252 to Banks et al, dated Dec. 20, 1994 and entitled "LOCKING PNEUMONEEDLE", discloses a pneumoneedle that comprises a cannula (20) mounted in a housing (12) (see FIG. 1). The housing (12) also contains a tubular protector (or "blunting member") (31) disposed within the cannula and movable between a retracted position in which the sharp tip of the cannula is exposed and a deployed position in which the blunt end (32) of the protector extends beyond the sharp tip of the cannula. The protector (31) is tubular and has a distal aperture (36) that is exposed when the protector is moved to the deployed position. There is also a proximal aperture (35) that opens to an internal fluid passageway portion of the housing (12). A fluid conduit (8) in the housing communicates with fluid passageway portion (18) and extends at an angle relative to the longitudinal axis of the needle cannula. The device is used for introducing an insufflating gas into the abdominal cavity of a patient via the fluid conduit. To determine whether the sharpened tip of the cannula, and therefore the distal aperture of the protector, are properly positioned, a saline/vacuum test must be performed. In this test, the device is primed with a small reserve of saline solution via the fluid conduit (8) and the device is inserted into the patient. The patient's abdomen is manipulated and if fluid communication has been established between the abdominal cavity and the device, the saline will be seen to surge. There is no indication or suggestion that the level of saline can be seen through the device housing, i.e., that the housing is translucent, or that the device may be adapted for intravenous use or that the fluid conduit be used for anything other than introducing an insufflating gas into the protector. In the medical field, pneumoneedles are considered to relate to a function that is disparate from that of intravenous fluid flow and the knowledge in the art pertaining to pneumoneedles is not seen as analogous or pertinent to intravenous needles.

U.S. Pat. No. 5,120,319 to Van Heugten et al, dated Jun. 9, 1992 and entitled "FLASH TUBE FOR INTRAVENOUS CATHETER", discusses some of the problems associated with flash chambers. As pointed out in this reference, when using small needles in small veins, quick flashback and quick reaction speed are more important than in larger veins. However, a larger flashback chamber is necessary when examining the blood flow to verify that it is continuing and thus there is a trade-off between large and small flash chambers. Van Heugten et al teaches a flash chamber having a capillary tube which will quickly fill with blood. Owing to the diffraction properties of the glass tube, the outside diameter of the tube appears to be red. This is combined with a conventional, larger, flash chamber allowing healthcare workers to verify continued flow of blood. While Van Heugten et al aids the healthcare worker in detecting the flash, the presented apparatus does not assist in successful venipuncture at angles close to parallel with the epidermis of the patient nor does Van Heugten et al teach any self-blunting mechanism.

U.S. Pat. No. 5,697,914 to G.L. Brimhall, dated Dec. 16, 1997 and entitled "CONTROL FORWARD/FLASHBACK FORWARD ONE HAND INTRODUCER NEEDLE AND CATHETER ASSEMBLY", is another non-self-blunting design which improves visibility of flash, by using an angled flash chamber. Brimhall also teaches a method for the healthcare worker/user to withdraw the needle within the catheter. However, Brimhall's needle is not automatically self-blunting, nor is there any method other than the angled nature of the flash chamber, to improve visibility of blood within the flash chamber. Finally, the wide fins projecting at various angles from the body of Brimhall's catheter assembly restrict motion at some orientations of the assembly.

It would be advantageous to provide a needle member with improved flash visualization which allows easy placement of the needle at any orientation even at angles parallel to the epidermis of the patient, and with easy access to a luer connection. It would further be advantageous if the catheter and needle assembly were held aligned while the catheter is removed from the needle assembly after insertion into the patient.

SUMMARY OF THE INVENTION

The invention provides a needle member comprising a needle cannula having a needle axis and a housing on which the needle cannula is mounted, the housing being at least partially translucent and dimensioned and configured to define a translucent flash chamber offset from but substantially parallel to the needle axis and in fluid communication with the needle cannula.

In another aspect, the invention provides a needle member comprising a needle cannula having a needle axis and a housing, the needle cannula mounted on the housing, the housing dimensioned and configured to define an access port offset from but substantially parallel to the needle axis.

Another aspect of the invention provides a needle member comprising a needle cannula having a needle axis and a housing on which the needle cannula is mounted, the housing being at least partially translucent and dimensioned and configured to define a translucent flash chamber in fluid communication with the needle cannula, and a display member disposed within the housing.

Another aspect of the invention provides a display member disposed within the flash chamber.

Another aspect of the invention provides a display member comprising a plurality of slats.

Yet another aspect of the invention provides a display member comprising a perforated tube disposed in the flash chamber.

Yet another aspect of the invention provides a blunting member comprising an elongate probe that has a blunt tip, the probe being disposed within the needle cannula. The probe is dimensioned and configured to be accommodated within the needle cannula while leaving the needle cannula open to fluid flow therethrough and the blunting member is movable between a retracted position in which the blunt tip of the blunting member is disposed within the needle cannula and a deployed position in which the blunt tip protrudes outwardly of and thereby blunts the tip of the needle cannula.

Yet another aspect of the invention provides a probe which is hollow and is in fluid communication with the flash chamber.

Yet another aspect of the invention provides a probe which is solid.

Yet another aspect of the invention provides a needle member comprising a needle cannula having a needle axis and a housing, the needle cannula mounted on the housing, the housing being at least partially translucent and dimensioned and configured to define a flash chamber substantially offset from but substantially parallel to the needle axis and in fluid communication with the needle cannula, and a display member having an enhanced blood surface area disposed within the housing.

BRIEF DESCRIPTION OF THE DRAWINGS

FIG. 2 is a cross-sectional view in elevation of the catheter and needle assembly of FIG. 1;

FIG. 3 is a view like that of FIG. 2 showing the needle assembly separating from the catheter and with the blunting member in its deployed position;

DETAILED DESCRIPTION OF THE INVENTION AND PREFERRED EMBODIMENTS THEREOF

Figure 1:
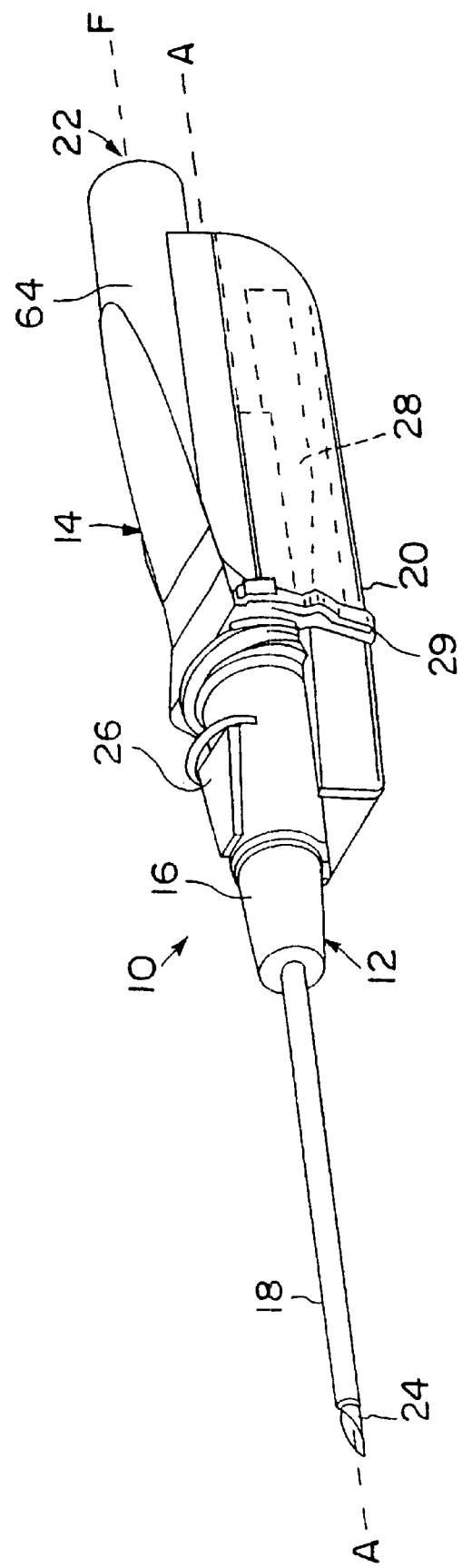
FIG. 1 is a perspective view of a catheter and needle assembly in accordance with a particular embodiment of the present invention.

The present invention provides a needle member comprising a needle cannula mounting in a housing designed to facilitate manipulation of the needle and to give the user a visual indication of proper placement of the needle for fluid transfer to or from a patient. At least part of the housing comprises a translucent material that defines a chamber, referred to herein and in the claims as a "flash chamber", that is in fluid communication with the needle cannula. In accordance with the present invention, and in contrast to the prior art in the field of intravenous needles, the housing is dimensioned and configured to define an elongate flash chamber which is disposed substantially parallel to, but offset from, the needle axis.

A flash chamber is typically much larger in cross-sectional dimension than the needle cannula to which it is connected. Accordingly, the flash chamber in a prior art needle member limits how closely to the surface of the user's skin the needle can be disposed during insertion because the chamber protrudes significantly in all radial directions about the axis of the needle. Even when the housing of a prior art catheter needle member is pressed against the skin, the needle therein is necessarily raised above the surface of the skin to a significant degree. In addition, a prior art needle member with an axially aligned flash chamber typically includes an access port for the connection of other fluid-transfer devices, such as a syringe, a luer connector, etc., to the needle member, and the access port is disposed axially on the flash chamber opposite from the needle. Therefore, devices being connected to the needle member must be aligned with the needle and, if connection is being made while the needle is in a patient's vein, the connecting device will have to be situated close to the patient's skin. This can make proper manipulation of the connecting device awkward.

In a needle member in accordance with one aspect of the present invention, the flash chamber is offset from the longitudinal axis of the needle cannula, and so protrudes principally in one particular direction from the needle cannula. In such configurations the flash chamber resides principally, i.e., protrudes most prominently, toward a particular radial direction about the needle axis, and leaves a potentially large region of minimal protrusion in other radial directions. By positioning part of a circumferentially large region of minimal protrusion towards the patient's skin, the user has greater freedom to angle the needle more closely against the patient's skin during use than if the center of the flash chamber were aligned with the needle axis. One embodiment of the present invention provides a needle member in which the radial distance from the longitudinal axis of the needle to the radial periphery of the housing about the flash chamber, i.e., the radial thickness of the housing, may be reduced in at least one radial direction, thus giving the housing a region of reduced radial thickness. In turn, when the needle assembly is placed with the reduced radial thickness adjacent the patient's skin, the entry angle required for the needle may be reduced or flattened. In some embodiments, this advantage may be realized even if the flash chamber is larger than in a prior art embodiment in which a smaller flash chamber is aligned with the needle axis. Thus an operator has an increased range of motion for finding and properly introducing a catheter into a vein of a patient. In other embodiments of the invention, the region of minimal protrusion or reduced radial thickness can be occupied by optional additional structures (such as the self-blunting mechanism disclosed below), so the invention permits the incorporation of the additional structures into the device without unduly increasing the radial thickness of the device. The additional structures therefore need not impose a greater limitation on the orientation of the needle than would be encountered with a conventional, prior art needle that lacked such structures. In addition, the flash chamber is typically cylindrical in configuration, or may otherwise define a longitudinal axis, e.g., as a result of having an elongate configuration, and the longitudinal axis of the flash chamber is substantially parallel to that of the needle. In other words, the flash chamber is not only offset from the needle axis, it is disposed with its longitudinal axis parallel to the needle axis.

Another, independent feature of the present invention is that the access port (or "luer access"), by which another fluid-flow device, such as a syringe, luer connector, etc., may be coupled to the needle member, is offset from the axis of the needle cannula. In a typical embodiment of this invention, this is achieved by positioning the access port on the off-set flash chamber, e.g., in line with the longitudinal axis of an off-set longitudinal flash chamber. However, this aspect of the invention may be practiced even in conjunction with a conventionally disposed (i.e., axially aligned) flash chamber, e.g., by disposing the access port on the side of the housing rather than at the end of the flash chamber. One advantage of having an off-set access port is that the access port is thereby distanced from the patient's skin, thus giving the user more freedom of movement in coupling another fluid-handling device to the needle member.

By providing the flash chamber on the needle member as described herein, the advantages of the present invention can be achieved with a conventional catheter. Once the catheter is properly placed, using the introducer needle and the associated flash chamber, the needle member can then be withdrawn from the catheter, which is then positioned for use in a conventional manner. Thus, the present invention provides a contrast to prior art catheter assemblies such as that shown in U.S. Pat. No. 5,697,914 to Brimhall (discussed above), which requires the use of a catheter that is specifically configured to incorporate the flash chamber.

Still another feature of the present invention is the incorporation into a needle housing of a display member. The display member is disposed in a visually discernible location in the path of fluid flow through the housing, optionally in a flash chamber, and is configured to provide an enhanced surface area on which fluid spreads and is visible. The fluid in the needle housing, e.g., blood, quickly wets the surface of the display member and thus augments the visual signal of fluid flow provided by the flash chamber.

Referring now to the drawings, a catheter and hypodermic needle assembly in accordance with a particular embodiment of the present invention is generally indicated at 10 of FIG. 1. The catheter and needle assembly 10 includes a catheter 12 and a needle member 14. Catheter 12 comprises a hub 16 from which extends a catheter tube 18. Needle member 14 includes a tubular needle cannula 24 (seen protruding from tube 18 of catheter 12) that is mounted in housing 20 and that has a longitudinal axis A.

Housing 20 defines a generally longitudinal, e.g., cylindrical, flash chamber 64 that is in fluid communication with needle cannula 24. The center of flash chamber 64 is positioned on axis F that is parallel to axis A and it can be seen that flash chamber 64 is therefore offset from axis A. Side portions 28 of housing 20 may be generally flat in shape so they may be easily gripped by a user such as a healthcare worker. In other embodiments, housing 20 and side portions 28 of housing 20 may be configured to yet further reduce the thickness of the device. Housing 20 may also include a cover mount 29 for mounting of a suitable cover (not shown), to further prevent stick wounds prior to use of catheter and needle assembly 10. Housing 20 of needle member 14 may also be formed of any suitably moldable and durable material such as a polyolefin plastic, polycarbonate, SAN (styrene-acrylonitrile copolymer) or ABS (acrylonitrile-butadiene-styrene copolymer) or the like. At least a portion of housing 20 that defines flash chamber 64 will be formed of a translucent material so that the user can see when blood has entered the device. As used herein and in the claims, the term "translucent material" is meant in a broad sense and should be understood to include transparent material or any other materials that permit visual perception of fluid therein. As shown in FIG. 1, tube 18 of catheter 12 is disposed over, and in co-axial relationship with, needle cannula 24, and the sharp tip of needle cannula 24 protrudes past the tip of tube 18. Assembly 10 is therefore ready for use. A mounting portion 26 may be provided on hub 16 for mating catheter 12 with an intravenous ("IV") tube (not shown). Hub 16 is typically formed from a polyolefin material.

Figure 1A:
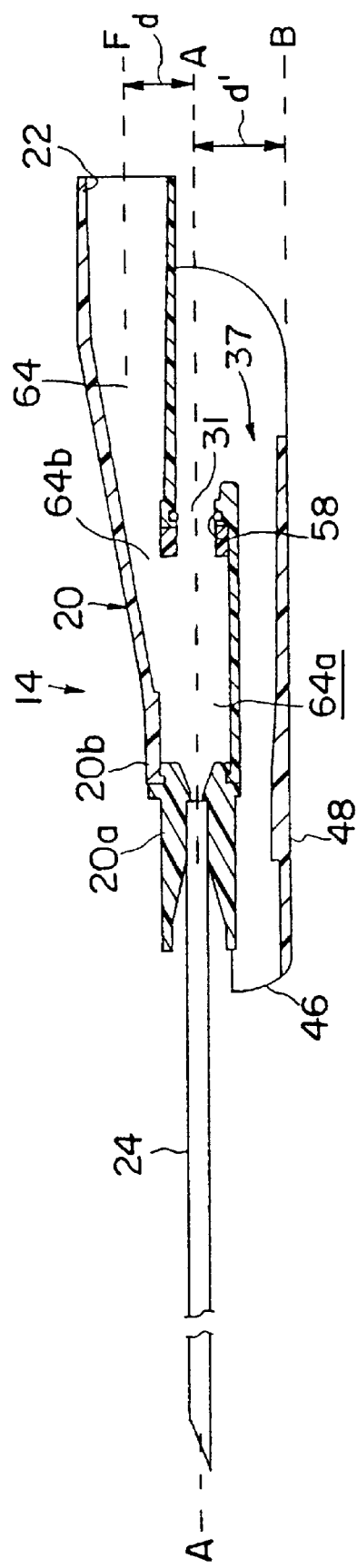
FIG. 1A is a cross-sectional view in elevation of the needle member of the assembly of FIG. 1.

In FIG. 1A, needle cannula 24 is seen in a cross-sectional view to be mounted in a needle hub 20a which, in turn, is secured to housing body 20b. Together, needle hub 20a and housing body 20b comprise housing 20. The proximal end of needle cannula 24 opens to an antechamber 64a in housing 20, which opens via a gap 64b to flash chamber 64. Flash chamber 64 is generally cylindrical in configuration and its center is disposed on an axis F that is substantially parallel to the longitudinal axis A of needle cannula 24. In accordance with the present invention, the center of flash chamber 64 is offset from axis A by a distance d. Flash chamber 64 therefore protrudes principally, i.e., it is offset, in a radial direction upward (as sensed in FIG. 1A) and not at all in the opposite radial direction or in the two lateral directions perpendicular thereto. It may also be clearly seen in FIG. 1A that the flow path between flash chamber 64 and needle cannula 24 through gap 64b must have a generally non-parallel orientation relative to axis A. In other words, for fluid to flow from needle cannula 24 to flash chamber 64, the flow path must have a radial component to it, i.e., the fluid must flow in a direction having a component perpendicular to axis A.

Figure 4:
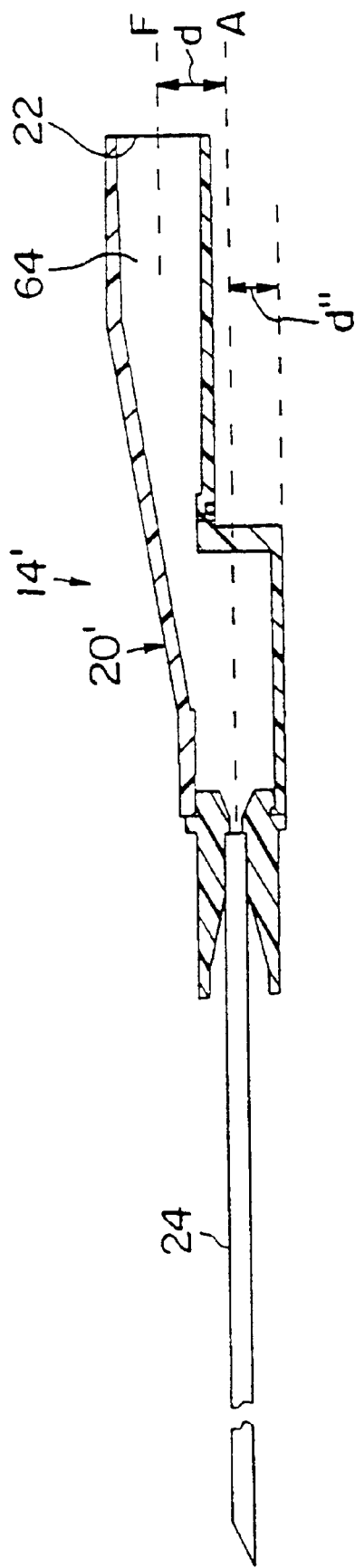
FIG. 4 is a cross-sectional view in elevation of a needle member in accordance with another embodiment of the present invention.

The embodiment shown in FIGS. 1 and 1A makes use of the upward offset of the flash chamber to permit the placement of optional additional structures in a direction opposite flash chamber 64, i.e., downward from axis A. Specifically, housing 20 is dimensioned and configured to accommodate a blunting mechanism within the space indicated at d' between axis A and periphery B, which is positioned radially opposite from flash chamber 64. To accommodate the blunting mechanism, housing 20 comprises a generally U-shaped channel 46 that defines a central passageway 37 and that has a flat outer surface 48 for contact with a patient's skin. Alternatively, either of side portions 28 could be disposed against the patient's skin to permit an even flatter angle of entry of the needle into the skin. In other embodiments, the blunting mechanism may be accommodated on either side of housing 20 or may be omitted, as shown in FIG. 4.

Figure 1B:
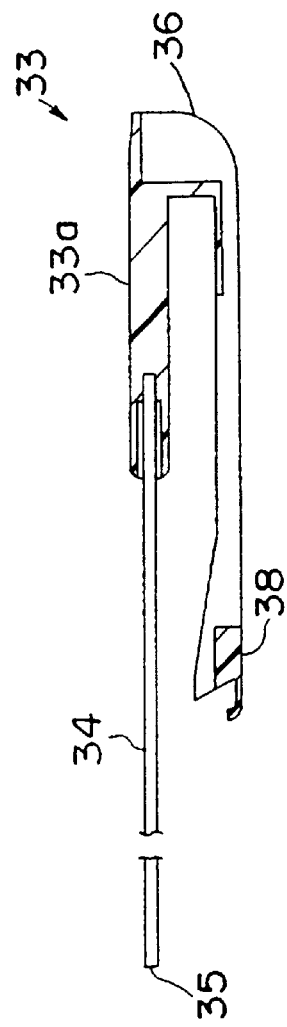
FIG. 1B is a cross-sectional view in elevation of a blunting member for use with the needle member of FIG. 1A.

Housing 20 defines a blunting member aperture 31 through which a blunting member 33 can be positioned for axial insertion into needle cannula 24. Blunting member 33 for use with needle cannula 24 of FIG. 1A is shown in FIG. 1B. Blunting member 33 comprises an elongate probe 34 having a blunt tip 35. Probe 34 is mounted in a mounting ferrule 33a that is dimensioned and configured to sealingly engage bushing 58 in blunting member aperture 31. Probe 34 is dimensioned and configured so that it can be inserted through aperture 31 and into needle cannula 24 so that, when mounting ferrule 33a is fully inserted in aperture 31, tip 35 will extend beyond, and thus obscure, the sharp tip of needle cannula 24, thus blunting the needle member 14. Probe 34 may be hollow or solid, but in either case it is configured so that it does not prevent the flow of fluid through needle cannula 24. Mounting ferrule 33a comprises part of a shuttle 36, which is dimensioned and configured to be received within passageway 37 and which comprises a latch portion 38 that is configured to engage the catheter hub as will be described further below.

FIG. 2 shows that catheter hub 16 includes a central bore 42 that is configured to receive needle member 14 therein. A reduced diameter portion of central bore 42 may include a sleeve 44, optionally formed of metal, for receiving needle cannula 24 and preventing damage to catheter hub 16 or to the tip of needle cannula 24 when catheter 12 is sliding over needle cannula 24 to engage needle hub 20a and probe 34.

FIG. 2 illustrates the catheter and needle assembly 10 in a sharpened configuration, i.e., with needle cannula 24 protruding from catheter tube 18 so that needle assembly 10 is ready for use in introducing catheter 12 into a patient's vein. Hub 16 of catheter 12, which is specially configured to engage latch portion 38 of shuttle 36, has positioned blunting member 33 in the retracted position, leaving the sharp tip of needle cannula 24 exposed. When venipuncture is achieved, blood enters needle cannula 24 and flows into hollow interior 60 of probe 34, then leaves probe 34 via aperture 62 and flows in a non-axial direction into flash chamber 64 via gap 64b. Housing 20 carries a schematically indicated flash plug 22a at access port 22 to prevent leakage. At least a portion of housing 20, defining flash chamber 64, is transparent or otherwise translucent so that the user can see when blood flows therein. Flash plug 22a is vented to allow air to escape but it is configured to prevent leakage of fluid. Flash plug 22a may be puncturable or removable to permit the optional introduction or withdrawal of fluids through flash chamber 64, if desired. In this way, once the user has confirmed venipuncture by visual inspection of flash chamber 64, access port 22 can be used for the introduction or withdrawal of fluids into or from the patient's vein via assembly 10 by another fluid-handling device connected thereto. When the necessary healthcare functions have been performed and it is desired to remove needle cannula 24 from the patient and leave catheter 12 in place for later use, needle member 14 can be withdrawn from catheter 12 (which may then be stoppered or connected to an IV line), whereby shuttle 36 is pulled forward due to the engagement of latch portion 38 with catheter 12, thus moving blunting member 33 forward to the deployed position and blunting tip 35 of needle cannula 24. As illustrated in FIG. 3, upon removal of catheter 12 from needle member 14, aperture 62 is moved out of communication with flash chamber 64 and sealed adjacent the interior bore of needle cannula 24.

In accordance with another embodiment of the invention, a needle member having an axially-displaced flash chamber can be employed without allowing for additional mechanisms, so that the needle member housing can have a radial region of reduced thickness relative to the needle axis. For example, FIG. 4 shows a particular embodiment of the invention in which a needle member 14' comprises a housing 20' in which needle cannula 24 is mounted. Housing 20' defines a flash chamber 64 and an access port 22. As with previously illustrated embodiments, flash chamber 64 is axially offset from needle axis A by distance d. However, housing 20' does not include the U-shaped channel designed to accommodate a blunting mechanism as in the embodiment of FIGS. 1–3. Accordingly, in the region radially opposite from flash chamber 64, needle member 14' presents a very small radial thickness d". This small radial thickness or protrusion in the region opposite from flash chamber 64 allows the healthcare worker to insert needle 24 at a very low angle relative to the patient's skin. At the same time, as mentioned above in connection with the embodiment of FIGS. 1 through 3, access port 22 will be situated above the patient's skin, providing convenient access for the healthcare worker and added safety and comfort to the patient. Needle member 14' can be used for the introduction of a conventional catheter the same way as described above for needle member 14. Similarly, the thickness of the needle member in directions generally lateral, e.g., perpendicular, to the radical direction of displacement of the flash chamber may be small as well.

Figure 4A:
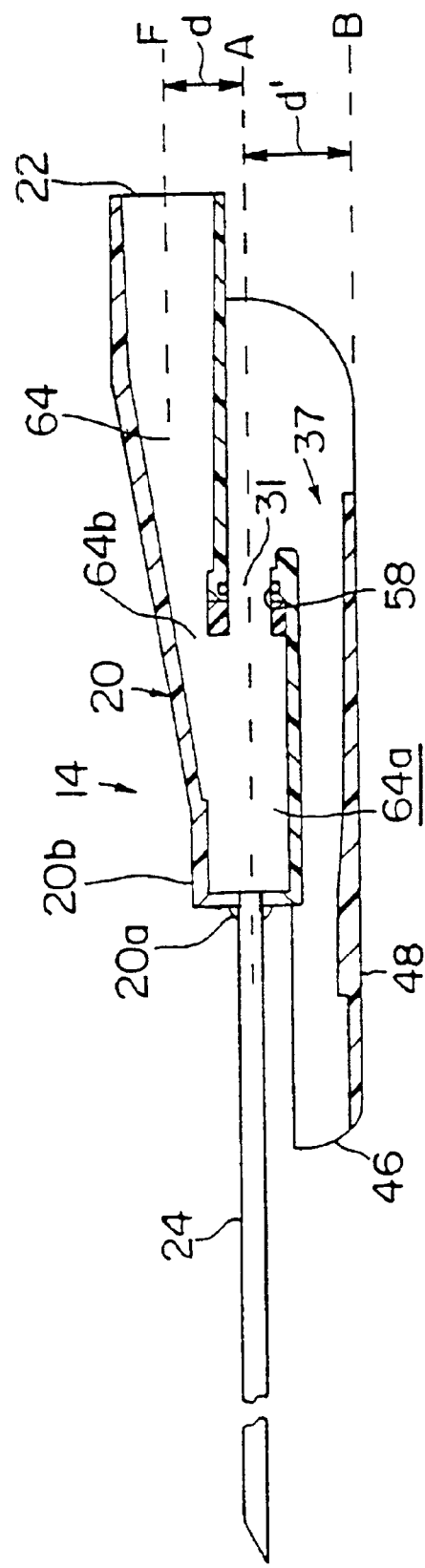
FIG. 4A is a cross-sectional view in elevation of a needle assembly in accordance with another embodiment of the present invention.

FIG. 4A illustrates another alternative embodiment of the invention. In this embodiment, needle hub 20a does not have the extended nose configuration.

Figure 5:
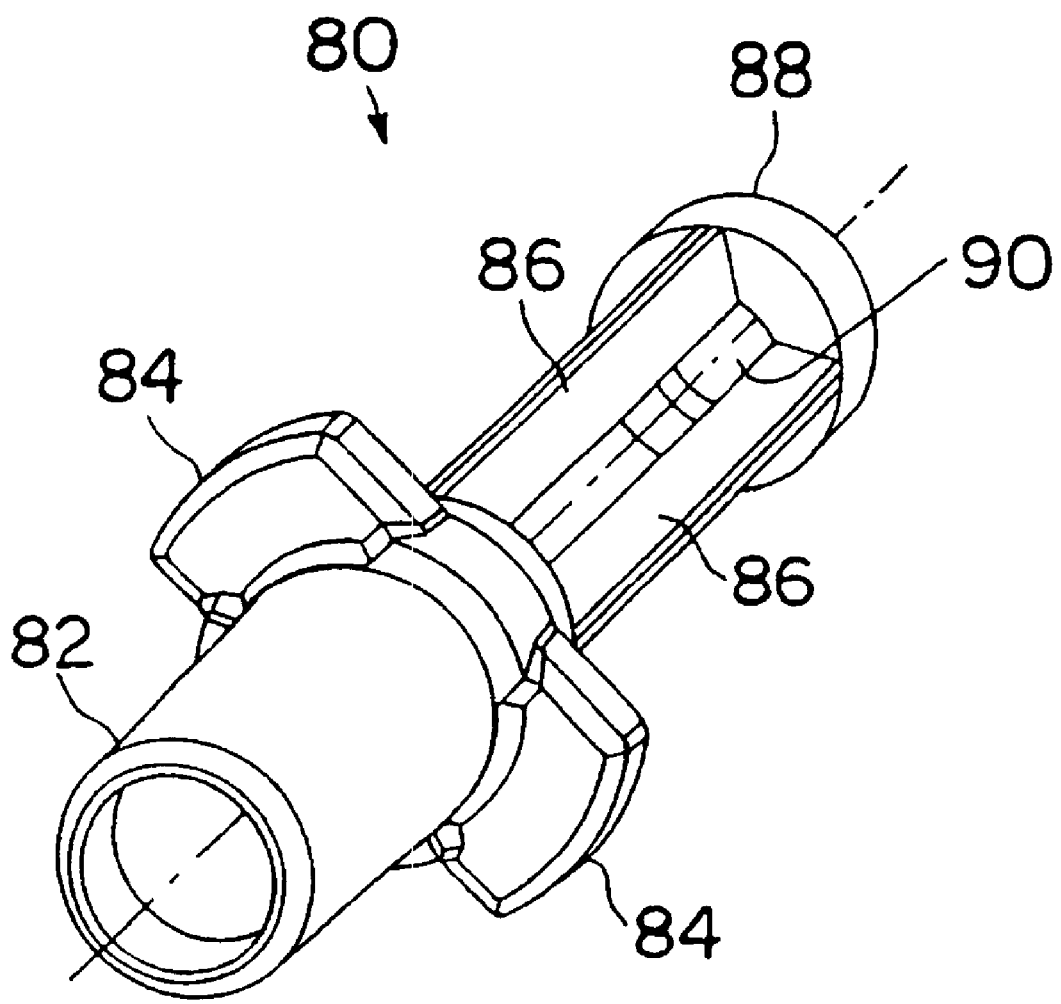
FIG. 5 is a perspective view of a display member according to a particular embodiment of the present invention.

Still another, independent, feature of the present invention relates to the positioning of a display member in a visually discernible location in the needle assembly, so that the display member is contacted by the fluid flowing therethrough. The display member is dimensioned and configured to have a higher surface area for contact by the fluid than the interior of the needle assembly in the vicinity where the display member is disposed. Since the fluid flowing through that portion of the device contacts a larger, and more visually discernible, surface area than it otherwise would in that region of the device, the display member of this aspect of the invention increases the visibility of the fluid. One example of a display member in accordance with this aspect of the present invention is shown in FIG. 5. Display member 80 comprises an optional mounting ferrule 82 which is generally cylindrical in shape and has an interior passage therethrough, and which is configured to receive a needle hub therein. Display member 80 further comprises optional mounting flanges 84 that are dimensioned and configured to engage the housing and secure display member 80 thereto. The aperture also opens rearward to where display member 80 comprises longitudinally-extending slats 86 which are interconnected via mounting ferrule 82. Slats 86 terminate at a sealing ring 88 that optionally forms an access aperture 90 dimensioned and configured to receive a blunting member and/or to facilitate fluid flow to or through the flash chamber.

Figure 6:
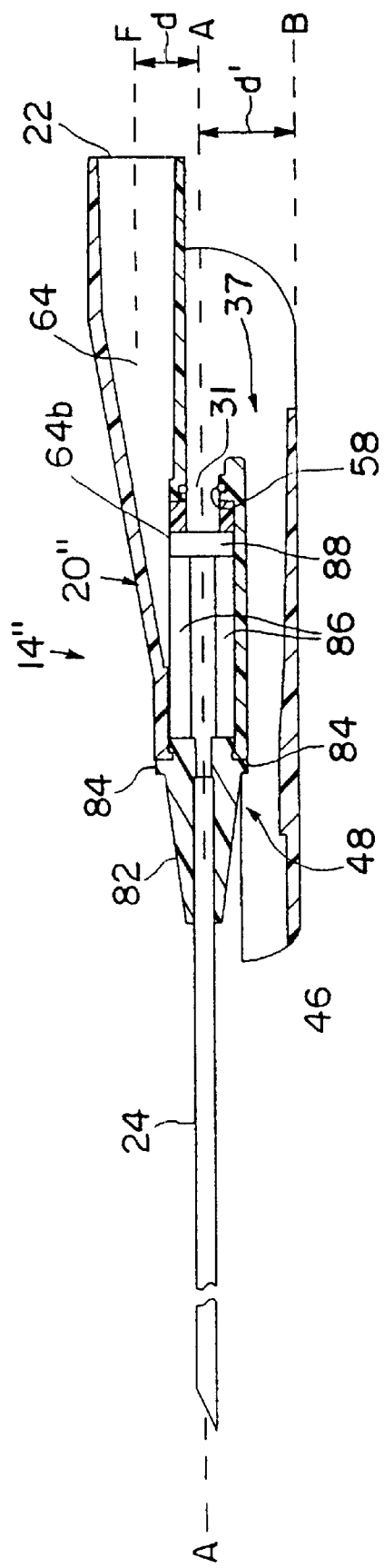
FIG. 6 is a schematic cross-sectional view of a needle member including the display member of FIG. 5.

FIG. 6 shows an alternative embodiment of needle member 14" in which display member 80 (FIG. 5) is mounted in a needle housing 20" in a region corresponding to antechamber 64a of needle member 14. Sealing ring 88 is positioned and sealed to the housing at blunting member aperture 31 so that access aperture 90 (FIG. 5) communicates with blunting member aperture 31. Access aperture 90 (FIG. 5) is dimensioned to receive probe 34 and mounting ferrule 33a and so does not interfere with the function of blunting member 33 (FIG. 1B). At the opposite end of display member 80, mounting flanges 84 and the portion of display member 80 rearward thereof sealingly engage housing 20". Mounting ferrule 82 extends forward from housing 20". Needle cannula 24 is mounted in mounting ferrule 82. The interior of needle cannula 24 opens to the interior of mounting ferrule 82. Accordingly, fluid such as blood, flowing from the patient through needle cannula 24, passes through mounting ferrule 82 and comes into contact with slats 86 that extend between mounting ferrule 82 and sealing ring 88. The blood quickly wets the surfaces of slats 86 upon entry into housing 20". The presence of display member 80 in housing 20" causes fluid initially entering the housing to be dispersed over a relatively large, visible surface area instead of allowing it to pool or agglomerate within the housing antechamber. Display member 80 provides a much higher visibly discernible surface area than does the interior of the antechamber in which it is positioned. By disposing the wetted surfaces of slats 86 in a translucent portion of the device, the user is provided with a visual indication that fluid is flowing into the device; that indication is provided more quickly and offers greater ease of visual recognition than with devices that are not equipped with an enhanced surface area display member and/or in which only the flash chamber is formed from translucent material. The improved visibility is achieved via the flash chamber and, if the antechamber is formed from translucent material, via the antechamber, before the fluid fills or even enters the flash chamber 64.

Figure 7A:
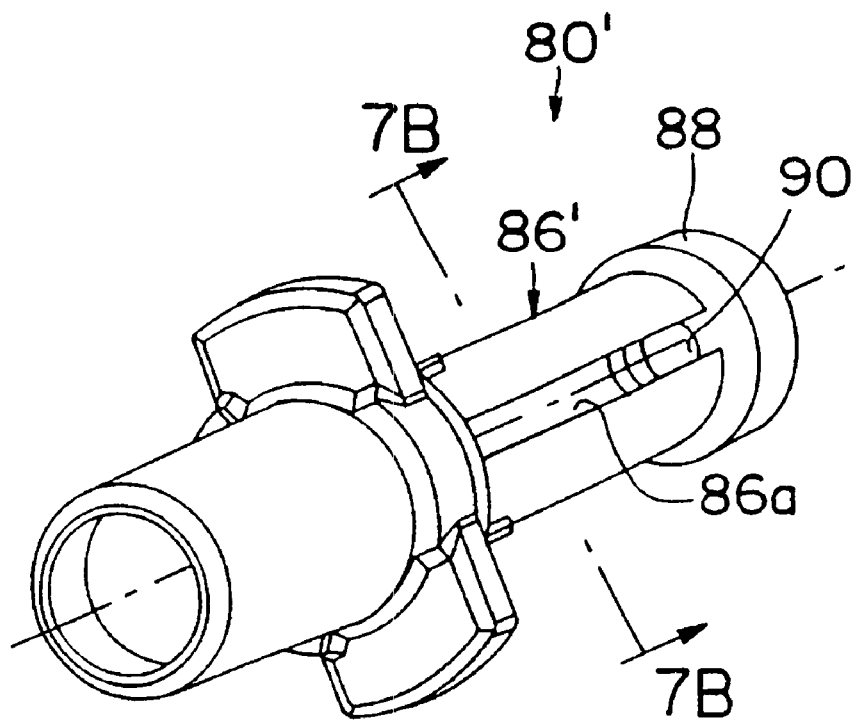
FIG. 7A is a perspective view of a display member according to another embodiment of the invention.
Figure 7B:
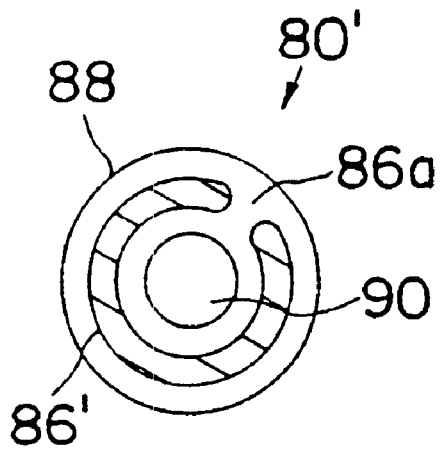
FIG. 7B is a cross-sectional view of the display member of FIG. 7A taken along line 7B—7B.

The display member may have any configuration that increases the visually discernible surface area within the needle member housing. The display member generally has a non-tubular configuration, i.e., it preferably is not configured as a simple, unperforated or unslotted tube. For example, instead of a plurality of slats, a display member in accordance with the present invention may comprise a longitudinally slotted or otherwise perforated cylinder, as illustrated in FIGS. 7A and 7B. FIG. 7A shows display member 80' having substantially the same configuration as display member 80 of FIG. 5, except that instead of slats 86, display member 80 comprises a slotted cylindrical portion 86' having a longitudinally extending slot 86a. Blood or another fluid flowing into the interior of portion 86' will exit via slot 86a and then wet the exterior surface of cylindrical portion 86' before filling the chamber within which display member 80' is disposed. Once again, the visible surface area on which blood disperses is enhanced. Since the effect of the display member derives principally from the surface area it provides inside a needle housing, the display member may optionally be an opaque structure.

It will be understood from the foregoing that the benefits of a display member can be obtained whether the chamber within which it is disposed is aligned with the needle cannula or is displaced from the axis of the needle. For example, in various embodiments, a display member may be employed in a needle member having either an aligned flash chamber or an off-set flash chamber to increase the visible surface area therein. According to still other embodiments, the display member may reside entirely within the needle housing and need not comprise either of a mounting ferrule for receiving a needle hub or an access aperture for receiving a blunting member.

While the invention has been described in detail with reference to particular embodiments thereof, upon a reading and understanding of the foregoing, numerous alterations to the described embodiments will occur to those skilled in the art, and it is intended to include such alterations, substitutions and equivalents within the scope of the appended claims.

What is claimed is:

1. A needle member comprising:
   a needle cannula having a needle axis; and
   a housing on which the needle cannula is mounted, the housing being at least partially translucent and dimensioned and configured to define a translucent flash chamber in fluid communication with the needle cannula: and
   a display member disposed within the housing, wherein the display member is disposed within the flash chamber.

2. The needle member of claim 1, wherein the display member comprises a perforated tube disposed in the flash chamber.

3. The needle member of claim 1, wherein the translucent flash chamber is offset from the needle axis.

4. The needle member of claims 3, wherein the translucent flash chamber is offset from but substantially parallel to the needle axis.

5. The needle member of claim 1, wherein the housing is dimensioned and configured to define an access port offset from the needle axis.

6. The needle member of claim 5, wherein the housing is dimensioned and configured to define an access port offset from but substantially parallel to the needle axis.

7. A needle member comprising:
   a needle cannula having a needle axis; and
   a housing on which the needle cannula is mounted, the housing being, at least partially translucent and dimensioned and configured to define a translucent flash chamber in fluid communication with the needle cannula; and
   a display member disposed within the housing, wherein the display member comprises a plurality of slats.

8. The needle member of claim 7, wherein the translucent flash chamber is offset from the needle axis.

9. The needle member of claim 8, wherein the translucent flash chamber is offset from but substantially parallel to the needle axis.

10. The needle member of claim 7, wherein the housing is dimensioned and configured to define an access port offset from the needle axis.

11. The needle member of claim 10, wherein the housing is dimensioned and configured to define an access port offset from but substantially parallel to the needle axis.

12. The needle member of claim 1 or claim 7, further comprising a blunting member comprising an elongate probe that has a blunt tip, the probe being disposed within the needle cannula, the probe being dimensioned and configured to be accommodated within the needle cannula while leaving the needle cannula open to fluid flow therethrough, the blunting member being movable between a retracted position in which the blunt tip of the blunting member is disposed within the needle cannula and a deployed position in which the blunt tip protrudes outwardly of and thereby blunts the tip of the needle cannula.

13. The needle member of claim 12, wherein the probe is hollow and is in fluid communication with the flash chamber.

14. The needle member of claim 12, wherein the probe is solid.

* * * * *